United States Patent
Delima et al.

(10) Patent No.: US 11,017,171 B2
(45) Date of Patent: May 25, 2021

(54) RELEVANCY AS AN INDICATOR FOR DETERMINING DOCUMENT QUALITY

(71) Applicant: INTERNATIONAL BUSINESS MACHINES CORPORATION, Armonk, NY (US)

(72) Inventors: Roberto Delima, Apex, NC (US); Andrew R. Freed, Cary, NC (US); Brien Muschett, Palm Beach Gardens, FL (US); Krishna Mahajan, Raleigh, NC (US); David Contreras, Willow Spring, NC (US)

(73) Assignee: International Business Machines Corporation, Armonk, NY (US)

( * ) Notice: Subject to any disclaimer, the term of this patent is extended or adjusted under 35 U.S.C. 154(b) by 63 days.

(21) Appl. No.: 16/434,112

(22) Filed: Jun. 6, 2019

(65) Prior Publication Data
US 2020/0387571 A1    Dec. 10, 2020

(51) Int. Cl.
*G06F 40/284*   (2020.01)
*G06N 5/02*     (2006.01)
*G06F 40/169*   (2020.01)

(52) U.S. Cl.
CPC .......... *G06F 40/284* (2020.01); *G06F 40/169* (2020.01); *G06N 5/025* (2013.01)

(58) Field of Classification Search
None
See application file for complete search history.

(56) References Cited

U.S. PATENT DOCUMENTS

| | | | |
|---|---|---|---|
| 7,308,116 B2 | 12/2007 | Harrington et al. | |
| 7,391,885 B2 | 6/2008 | Harrington et al. | |
| 7,797,344 B2 | 9/2010 | Kaul et al. | |
| 7,835,902 B2 | 11/2010 | Gamon et al. | |
| 8,131,559 B2 | 3/2012 | Robinson | |
| 8,874,549 B2 | 10/2014 | Tunkelang et al. | |
| 9,286,379 B2 | 3/2016 | Yang et al. | |
| 2007/0078670 A1* | 4/2007 | Dave | G06F 40/253 705/347 |
| 2012/0123767 A1* | 5/2012 | Ananthanarayanan | G06F 40/253 704/9 |
| 2013/0060793 A1* | 3/2013 | Bandyopadhyay | G16H 10/60 707/755 |
| 2016/0026634 A1 | 1/2016 | Allen et al. | |
| 2016/0098403 A1* | 4/2016 | Lee | G06F 16/93 707/749 |

(Continued)

FOREIGN PATENT DOCUMENTS

EP    1503338 A3    12/2005

OTHER PUBLICATIONS

Contreras et al., "Cognitive Document Quality Determination With Automated Heuristic Generation," Application and Drawings, filed Nov. 2, 2018, 34 Pages, U.S. Appl. No. 16/179,371.

(Continued)

*Primary Examiner* — Stella L. Woo
(74) *Attorney, Agent, or Firm* — Rakesh Roy

(57) ABSTRACT

A method, computer system, and a computer program product for relevancy-based document quality assessment is provided. The present invention may include computing a document quality score based on at least one container relevancy score determined based on at least one domain link to a domain knowledge base.

19 Claims, 6 Drawing Sheets

(56) References Cited

U.S. PATENT DOCUMENTS

2020/0293712 A1* 9/2020 Potts ..................... G16H 10/60

OTHER PUBLICATIONS

Mell et al., "The NIST Definition of Cloud Computing," National Institute of Standards and Technology, Sep. 2011, p. 1-3, Special Publication 800-145.

* cited by examiner

RELEVANCY AS AN INDICATOR FOR DETERMINING DOCUMENT QUALITY

BACKGROUND

The present invention relates generally to the field of computing, and more particularly to cognitive processing.

Cognitive systems implement natural language processing (NLP) and other machine learning technologies to synthesize large sources of data content, e.g., electronic documents, in order to generate hypotheses, recommendations, and/or answers to specific input questions. The quality of a given document may play an important role in the ability of a cognitive system to further process and understand the contextual meaning of a span of text in the given document.

SUMMARY

Embodiments of the present invention disclose a method, computer system, and a computer program product for relevancy-based document quality assessment. The present invention may include computing a document quality score based on at least one container relevancy score determined based on at least one domain link to a domain knowledge base.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
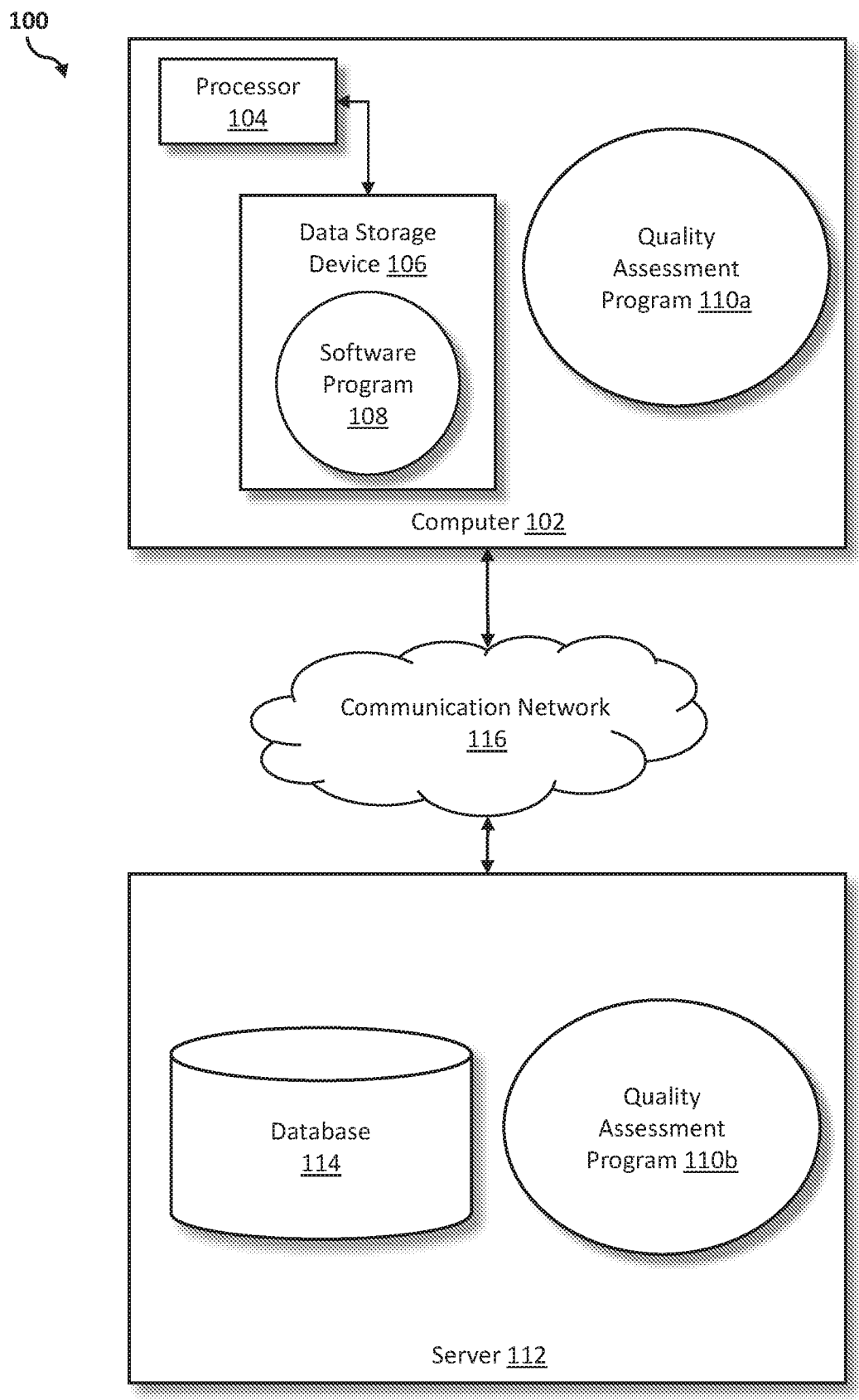
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language, or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for relevancy-based document quality assessment. As such, the present embodiment has the capacity to improve the technical field of cognitive processing by providing a document quality assessment model adapted to compute a quality score of a document (e.g., electronic document) based on the relevancy of individual spans of text to the overall meaning of the document. More specifically, a quality assessment program may identify one or more containers (e.g., grammatical structures representing sections, subsections, paragraphs, sentences, and list items) in a document. Then, the quality assessment program may assign an individual quality score to each of the containers based on document quality heuristics. Next, the quality assessment program may assign an individual relevancy score to each of the containers based on the frequency of domain-specific mentions in the respective containers. Thereafter, the quality assessment program may compute the quality score for the document based on the individual quality scores and relevancy scores associated with each of the containers in the document.

As previously described, cognitive systems implement natural language processing (NLP) and other machine learning technologies to synthesize large sources of data content, e.g., electronic documents, in order to generate hypotheses, recommendations, and/or answers to specific input questions. The quality of a given document may play an important role in the ability of a cognitive system to further process and understand the contextual meaning of a span of text in the given document.

Generic document quality assessment models may not be suitable to provide accurate quality assessment when dealing with a heterogeneous document set including varied grammatical structures. Certain document features like lack of complete sentences may be reliable indicators of poor document quality in some document sets and poor indicators in other document sets where lack of complete sentences are known and expected features of the document. In some instances, a document may include specific low-quality (or low-fidelity) spans of text in addition to other good or high-quality (or high-fidelity) spans of text. A purely document-level quality approach (e.g., generic document quality assessment model) may not provide the granularity required for masking only pieces of low-quality data (e.g., spans of text that may not be relevant to the understanding of the document).

For instance, in electronic medical records, a document (e.g., clinician note) may include well-formed narrative text, incomplete sentences or fragments, and informal language and shorthand. A general-purpose metric using a document-level quality approach (e.g., generic document quality assessment model), may assign a low-quality score to the clinician note due to the clinician note including shorter or more incomplete sentences than "typically good" documents; however, the clinician note may be completely in line with "typical" electronic medical records.

Therefore, it may be advantageous to, among other things, provide a way to determine the structure of a document and identify low-fidelity and high-fidelity spans of text in the document. It may be further advantageous to determine or adjust a document quality score (e.g., overall document quality) based on the relevancy of the low-fidelity and high-fidelity spans of text in the document. Thus, it may be advantageous to provide not just a generic document quality assessment model to determine if a document is a "good" document, but instead provide a tailored, relevancy-based document quality assessment model to determine if a document is a "good" document given the unstructured text contained in the document and the relevancy of the identified low-quality spans of text.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a quality assessment program 110a. The networked computer environment 100 may also include a server 112 that is enabled to run a quality assessment program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 4, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the quality assessment program 110a, 110b may interact with a database 114 that may be embedded in various storage devices, such as, but not limited to a computer/mobile device 102, a networked server 112, or a cloud storage service.

Figure 2:
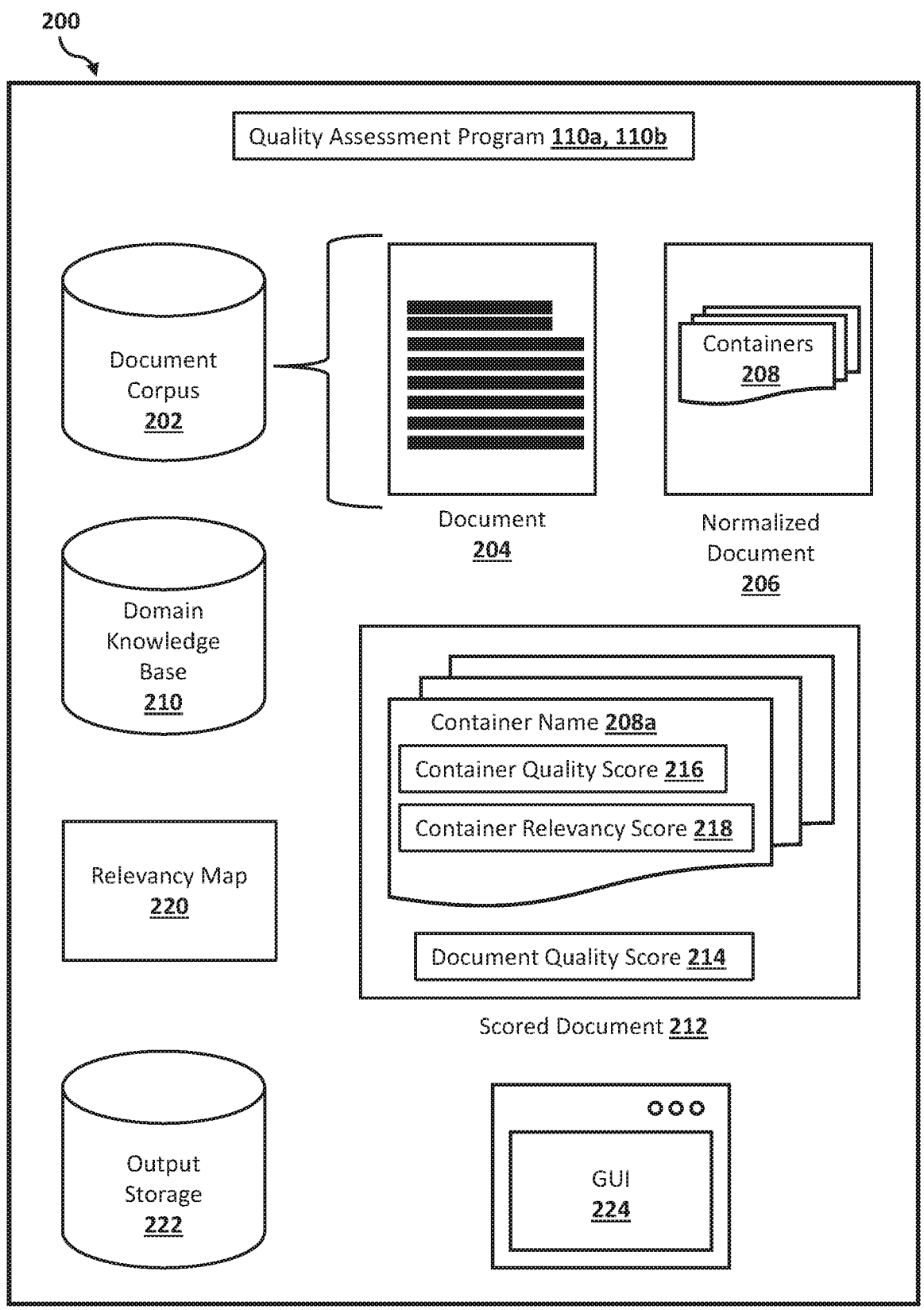
FIG. 2 is a block diagram of a quality assessment system according to at least one embodiment.

Referring now to FIG. 2, a block diagram illustrating a quality assessment system 200 according to at least one embodiment is depicted.

According to one embodiment, the quality assessment system 200 may be provided in the networked computer environment 100 and may be implemented on one or more client computers 102 and/or one or more server computers 112 to compute a document quality score based on the quality score and relevancy score of individual spans or portions (e.g., containers) of the document.

The quality assessment system 200 may generally include the quality assessment program 110a, 110b, a document corpus 202, one or more documents 204, one or more normalized documents 206, one or more containers 208 of the normalized document 206, a domain knowledge base 210, a scored document 212 including a document quality score 214 computed based on a container quality score 216 and a container relevancy score 218 for each container 208 (having a container name 208a) identified in the scored document 212, a relevancy map 220, an output storage 222, and a graphical user input (GUI) 224.

The quality assessment program 110a, 110b may include a single computer program or multiple program modules or sets of instructions being executed by the processor of the client computer 102/server computer 112. The quality assessment program 110a, 110b may include routines, objects, components, logic, data structures, and so on that may perform particular tasks or implement particular abstract data types. The quality assessment program 110a, 110b may be practiced in distributed cloud computing environments where tasks are performed by remote processing devices that may be linked through the communication network 116.

The quality assessment program 110a, 110b may provide a workflow (e.g., events, tasks, or instructions that may be executed by the processor of the client computer 102/server computer 112) to enable a user to access the document 204 stored in the document corpus 202, convert the document 204 into the normalized document 206, identify one or more containers 208 in the normalized document 206, and provide, in the scored document 212, the document quality score 214 of the document 204 calculated based on the container quality score 216 and the container relevancy score 218 of the one or more containers 208 identified in the normalized document 206 version of the document 204.

According to one embodiment, the document corpus 202 may include a repository or collection of documents 204. In at least one embodiment, the document corpus 202 may be stored in or implemented as part of the data storage device 106 of the client computer 102 or the database 114 of the server computer 112. In another embodiment, the document corpus 202 may be stored remotely in a cloud computing environment.

According to one embodiment, the documents 204 may include electronic documents, files, or data for processing and analysis by the quality assessment program 110a, 110b. In one example, the documents 204 may include electronic medical records (e.g., clinician notes) or other healthcare documents (e.g., pathology reports) for integration into a cognitive system. In at least one embodiment, the documents 204 may include unstructured data or a mix of structured and unstructured data, such as, for example, hypertext markup language (HTML) files or portable document format (PDF) files.

According to one embodiment, the documents 204 may be normalized (e.g., cleaned, converted, reduced to a common form) to the normalized documents 206 before further processing and analysis by the quality assessment program 110a, 110b. In at least one embodiment, the normalized documents 206 may be stored in the document corpus 202. When normalizing the documents 204, the text may be extracted from markup, such as HTML and PDF. In one instance, if the document 204 is an HTML file, a normalized output, for example the normalized document 206, may include a plain text file. In one embodiment, the normalization process of the document 204 may remove the HTML tags, JavaScript Object Notation (JSON), and any other markup language included in the document 204. In another instance, if the document 204 is a PDF file, the normalization process may extract the text and remove any markup, images, and other non-text objects in the document 204. Thus, according to at least one embodiment, the normalized document 206 may include a version of the document 204 (e.g., original document) including the same or substantially the same textual content.

According to one embodiment, the normalized document 206 may include spans of text organized into one or more containers 208. The containers 208 may represent grammatical structures such as, sections, subsections, paragraphs, sentences, and list items. In one embodiment, the containers 208 may include malformed text in the form of sentence fragments, such as, checklists or string blobs (e.g., cryptic syntax, markup language). The quality assessment program 110a, 110b may identify the containers 208 in the normalized document 206 and determine the quality (e.g., container quality score 216) and potential relevancy (e.g., container relevancy score 218) of each of the containers 208 to the overall meaning of the document 204. Although the containers 208 are identified in the normalized document 206 in FIG. 2, it is contemplated that the containers 208 are also provided in the document 204 since the normalized document 206 is a version of the document 204 as previously described. As such, the containers 208 may be referred to herein as being associated with the document 204 and the normalized document 206.

According to one embodiment, the container quality score 216 of each container 208 may be based on document quality heuristics. In one embodiment, a non-exhaustive list of document quality heuristics may include, for example, the percentage of valid characters, valid words, and complete sentences in the container 208. In another embodiment, the document quality heuristics may also consider, for example, number of irrelevant tags or markup language (e.g., HTML, JSON), number of blank spaces between sentences, and number of blank spaces between tokens.

According to one embodiment, the container quality score 216 of each container 208 may be calculated in range from 0-1.0, where 0-0.4 may indicate poor quality, 0.41-0.7 may indicate fair quality, and 0.71-1.0 may indicate good quality. In another embodiment, any suitable range (e.g., 0-100) may be used to indicate the container quality score 216 of the containers 208.

According to one embodiment, each container 208 may be assigned a container relevancy score 218 which may determine the impact the container quality score 216 of the container 208 may have on the document quality score 214. In one embodiment, the domain knowledge base 210 may be accessed to determine the relevancy of the containers 208 in the normalized document 206.

According to one embodiment, the domain knowledge base 210 may include a source of domain-specific information. A domain may include a technical, professional, or academic field having a corresponding knowledge base. In one embodiment, the domain may include a healthcare domain and the corresponding domain knowledge base may include healthcare-related documents and sources of information. The domain knowledge base 210 may be stored in or implemented as part of the data storage device 106 of the client computer 102 or the database 114 of the server computer 112. In another embodiment, the domain knowledge base 210 may be stored remotely in a cloud computing environment.

According to one embodiment, the relevancy of the containers 208 may be determined based on domain links to the domain knowledge base 210. In one embodiment, the domain links may include one or more domain-specific mentions (e.g., terms and phrases relevant to the domain) identified in the containers 208 and matched with data stored the domain knowledge base 210. In at least one embodiment, the domain-specific mentions may also include domain-specific contextual clues.

The quality assessment program 110a, 110b may perform lexical analysis on the containers 208 to convert a sequence of characters (e.g., the span of text) into a sequence of tokens (e.g., words). Thereafter, the domain knowledge base 210 may be accessed to determine if the sequence of tokens in the containers 208 includes domain-specific mentions and/or domain-specific contextual clues. In one instance, if the domain knowledge base 210 is healthcare related, the lexical matching may determine that the terms "neuropathy," "tumor," and "3 cm" identified in a given container 208 are domain-specific mentions. In another instance, the lexical matching may determine that the phrases "patient complains of," "patient had," and "completed" identified in a given container 208 are domain-specific contextual clues.

In one embodiment, the container relevancy score 218 may be calculated based on the domain links to the domain knowledge base 210, which may include for example, a frequency/density of relevant mention types (e.g., domain-specific mentions and/or domain-specific contextual clues), a presence of rare mention types, and a combination of mention types (e.g., combination of relevant and rare mention types). In one embodiment, a rare mention type may comprise a more specific or niche category of the relevant mention type. For example, in an oncology domain, the term "cancer" and the phrase "small cell squamous lung cancer" may both be considered relevant mention types; however, the phrase "small cell squamous lung cancer" may also be considered a rare mention type.

According to one embodiment, the container relevancy score 218 of the container 208 may be revised based on the associated container name 208a. In one embodiment, the container name 208a may be identified based on a header text of the container 208 and may be mapped to a pre-determined container relevancy. In at least one embodiment, the quality assessment program 110a, 110b may store pre-existing knowledge of document content associated with container names in the relevancy map 220. The relevancy map 220 may be used to determine the relevancy of the container 208 having the container name 208a similar to container names included in the relevancy map 220. In one embodiment, the quality assessment program 110a, 110b may maintain the relevancy map 220 including pre-determined container relevancy data linked to container names. For example, the relevancy map 220 may indicate that in a pathology report, "Gross Description" sections are inherently noisy and of little value. As such, if the document 204 is determined to be a pathology report, the quality assessment program 110a, 110b may set the container relevancy score 218 of the container 208 having the container name 208a "Gross Description" to 0 so that the container quality score 216 of the container 208 does not impact the document quality score 214. In another example involving a pathology report, the relevancy map 220 may indicate that "Diagnosis" sections are important. As such, if the document 204 is determined to be a pathology report, the container relevancy score 218 of the container 208 having the container name 208a "Diagnosis" may be determined based on the frequency/density of the domain-specific mentions and/or domain-specific contextual clues, presence of rare mention types, and a combination of mention types, as detailed above.

According to one embodiment, the container relevancy score 218 of each container 208 may be calculated in range from 0-1.0, where 0-0.4 may indicate poor relevancy, 0.41-0.7 may indicate fair relevancy, and 0.71-1.0 may indicate good relevancy. In another embodiment, any suitable range (e.g., 0-100) may be used to indicate the container relevancy score 218 of the containers 208.

According to one embodiment, the document quality score 214 (e.g., document-level quality score) may be provided in the scored document 212. In one embodiment, the document quality score 214 may be calculated by combining the container quality 216 and the container relevancy score 218 of each container 208. In one embodiment, if the normalized document 206 includes multiple containers 208, each container 208's final container quality score 216 may be fed into the parent container (e.g., quality score of subsection container fed into quality score of section container).

In one embodiment, the document quality score 214 may be calculated using a weighted average algorithm, for example: weighted average of (container_relevancy_score*container_quality_score), where the container relevancy score 218 may be applied as the weight. As such, the containers 208 with higher container relevancy scores 218 (high weight) may contribute more to the document quality score 214 (weighted average) than containers 208 with lower container relevancy scores 218 (low weight).

According to one embodiment, the document quality score 214 may be calculated in range from 0-1.0, where 0-0.4 may indicate poor document quality, 0.41-0.7 may indicate fair document quality, and 0.71-1.0 may indicate good document quality. In another embodiment, any suitable range (e.g., 0-100) may be used to indicate the document quality score 214.

According to one embodiment, the output (e.g., scored document 212) of the quality assessment program 110a, 110b may be stored in the output storage 222 for further processing (e.g., by the cognitive system). In one embodiment, the scored documents 212 may be labeled (e.g., poor, fair, good) in the output storage 222. In another embodiment, the quality assessment program 110a, 110b may set (or enable the user to set) a quality threshold (e.g., 0.5-1.0). Thereafter, the quality assessment program 110a, 110b may filter out (e.g., discard) the scored documents 212 that fall below the quality threshold and only store, in the output storage 222, the scored documents 212 that meet the quality threshold.

In one embodiment, the output storage 222 may be stored in or implemented as part of the data storage device 106 of the client computer 102 or the database 114 of the server computer 112. In another embodiment, the output storage 222 may be stored remotely in a cloud computing environment.

According to one embodiment, the quality assessment program 110a, 110b may implement the GUI 224 and display a digital representation of the scored document 212, for example, via computer display monitor 924 (as will be discussed with reference to FIG. 4). According to one embodiment, the GUI 224 may display the scored document 212 including annotations of the containers 208 as well as the container quality score 216, container relevancy score 218, and document quality score 214. In another embodiment, the GUI 224 may highlight one or more containers 208 that most impacted (e.g., high container relevancy score 218) the document quality score 214. In at least one embodiment, the GUI 224 may also highlight the domain-specific mentions/domain-specific contextual clues in the containers 208 of the scored document 212.

According to the present embodiment, a user using a client computer 102 or a server computer 112 may use the quality assessment program 110a, 110b (respectively) of the quality assessment system 200 to compute the document quality score 214 based on the container quality score 216 and container relevancy score 218 of individual containers 208 of the document 204. The quality assessment method is explained in more detail with respect to FIG. 2 (detailed above) and FIG. 3 (detailed below).

According to one embodiment, the quality assessment method may generally include computing a document quality score based on one or more container relevancy scores determined based on one or more domain links to a domain knowledge base. In one embodiment, the quality assessment method may include determining one or more container quality scores associated with a document. In another embodiment, the quality assessment method may include determining one or more container relevancy scores associated with the document based on identifying one or more domain links to the domain knowledge base. In at least one embodiment, the quality assessment method may include computing the document quality score based on the one or more container quality scores and the one or more container relevancy scores.

Figure 3:
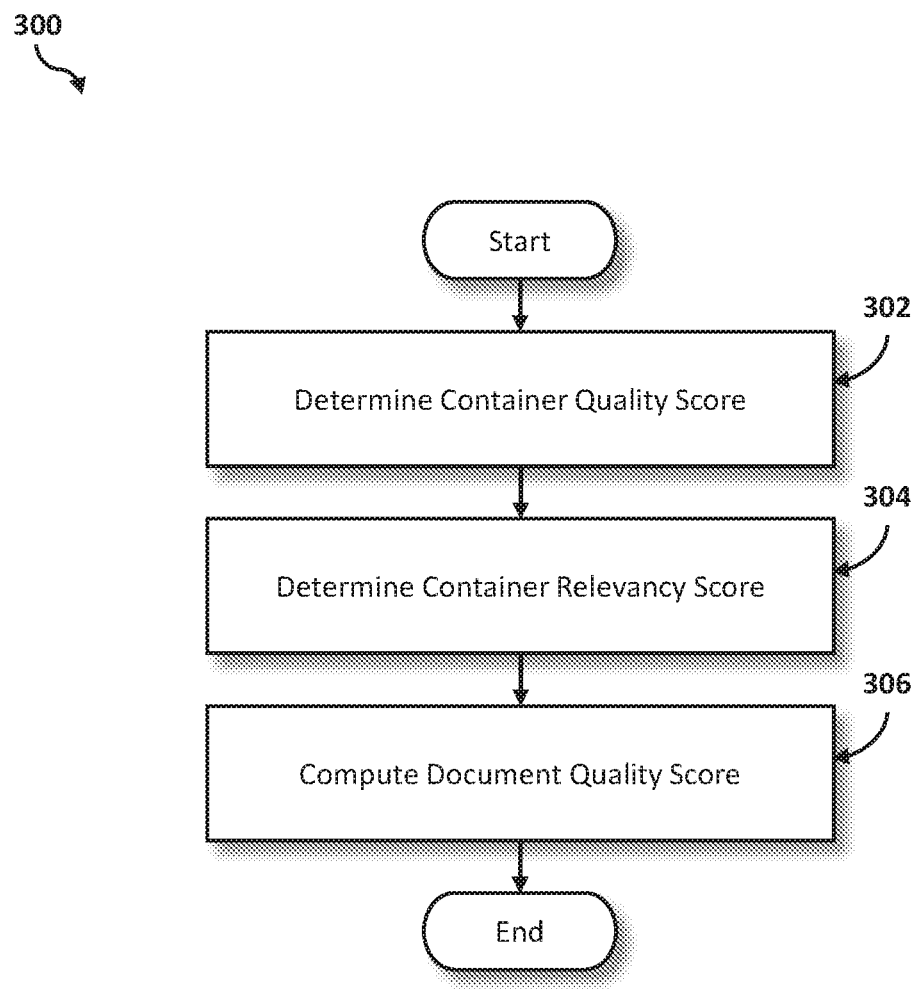
FIG. 3 is an operational flowchart illustrating a process for quality assessment according to at least one embodiment.

Referring now to FIG. 3, an operational flowchart illustrating the exemplary quality assessment process 300 used by the quality assessment program 110a and 110b, as described in connection to FIG. 2, according to at least one embodiment is depicted.

At 302, a container quality score is determined. According to one embodiment, the quality assessment program 110a, 110b may determine container quality scores (e.g., container quality score 216) for respective containers (e.g., containers 208) associated with a document (e.g., document 204). Initially, the quality assessment program 110a, 110b may prompt a user to select one or more documents from the document corpus (e.g., document corpus 202) for use in the quality assessment process 300. In response, the quality assessment program 110a, 110b may receive one or more selections from the user interacting with the client computer 102 or a server computer 112. In another embodiment, the quality assessment program 110a, 110b may automatically determine the one or more documents to select in the document corpus for use in the quality assessment process 300.

Then, as previously described, the quality assessment program 110a, 110b may normalize the documents into plain text files (e.g., normalized document 206) including one or more spans of text organized into containers (e.g., containers 208). Next, the quality assessment program 110a, 110b may run document quality heuristics to determine the quality score (e.g., container quality score 216) for each container identified in the normalized document. According to one embodiment, the document quality heuristics may include, for example, the percentage of valid characters, valid words, and complete sentences identified in the containers. According to another embodiment, the document quality heuristics may also include, for example, number of irrelevant tags or markup language (e.g., HTML, JSON), number of blank spaces between sentences, and number of blank spaces between tokens identified in the containers. Based on the document quality heuristics, the quality assessment program 110a, 110b may calculate and provide the quality score (e.g., range from 0-1.0, where 0-0.4 may indicate poor quality, 0.41-0.7 may indicate fair quality, and 0.71-1.0 may indicate good quality) for each of the containers.

In one example, the quality assessment program 110a, 110b accesses the document 204 in the document corpus 202 and normalizes the document 204 to provide the normalized document 206. The quality assessment program 110a, 110b identifies four containers 208 in the normalized document 206. Example containers 1-4 of the normalized document are provided below in respective TABLES 1-4:

TABLE 1

EXAMPLE CONTAINER 1 OF NORMALIZED DOCUMENT

Diagnosis
<p><br/><li><ul>We find an abnormal lesion in the right lung. >$% the #$& metastasis €
</ul></li>

The quality assessment program 110a, 110b runs document quality heuristics in container 1 provided in TABLE 1 (above) and determines a container quality score 216 of 0.4 out of 1.0 (poor quality) due to the number of irrelevant tags and markup language identified in the container 1.

TABLE 2

EXAMPLE CONTAINER 2 OF NORMALIZED DOCUMENT

Gross description
wrnkbn sfdgklmsdfb s sfgmslfg s fsfbsfl bsflb sf,bs;fb sb lsdf;b sbf sflb;sfdbdsbb.

Next, the quality assessment program 110a, 110b runs document quality heuristics in container 2 provided in TABLE 2 (above) and determines a container quality score 216 of 0.0 out of 1.0 (poor quality) due to a lack of words identified in the container 2.

TABLE 3

EXAMPLE CONTAINER 3 OF NORMALIZED DOCUMENT

COMMENTS
The cell block preparation was contributory toward making the above diagnosis.
Staff:AA
SR:10S, 2CB
MDL CB:50-300
MDL Pap:3
MDL DQ:3
4/26/2015 11:37 AM
Some tests reported here may have been developed and performance characteristics determined by The Electric Mayhem Pathology and Laboratory Medicine. These tests have not been specifically cleared or approved by the U.S. Food and Drug Administration. <SigArea><Sig>2
Entire report and diagnosis completed and released by: Dr. John 11111 Apr 26, 2015
</Sig></SigArea>

Then, the quality assessment program 110a, 110b runs document quality heuristics in container 3 provided in TABLE 3 (above) and determines a container quality score 216 of 0.2 out of 1.0 (poor quality) due to the irrelevant tags and markup language identified in the container 3.

TABLE 4

EXAMPLE CONTAINER 4 OF NORMALIZED DOCUMENT

PHYSICAL EXAMINATION: GENERAL: The examination was performed by Dr.
**NAME[ZZZ], as per
the request of the patient, given his **NAME[SSS RRR] beliefs. Well developed man in no
acute distress. ECOG 1. HEAD/NECK: Anicteric conjunctivae. Pupils are equal, round, react to
light.
Oropharynx clear without thrush, mucositis or other oral lesions. Neck is supple and nontender.
NODES: No palpable peripheral lymphadenopathy HEART: Regular rate and rhythm, no
murmurs,
rubs, gallops LUNGS: Clear to auscultation bilaterally, no wheezes or rhonchi. ABDOMEN:
Soft,
nontender, nondistended, normoactive
bowel sounds, no palpable masses EXTREMITIES: No lower extremity edema or swelling
NEURO:
Grossly nonfocal examination, no focal deficits, normal gait SKIN: No rash or jaundice Then, the quality assessment program 110a, 110b runs document quality heuristics in container 4 provided in TABLE 4 (above) and determines that container 4 includes sections and subsections that have been collapsed, long run-on sentences, and poor grammatical structure. As such, the quality assessment program 110a, 110b calculates a container quality score 216 of 0.3 out of 1.0 (poor quality) for container 4.

Then at 304, a container relevancy score is determined. According to one embodiment, the quality assessment program 110a, 110b may determine container relevancy scores (e.g., container relevancy score 218) for respective containers (e.g., containers 208) associated with the document (e.g., document 204). The container relevancy scores assigned to the respective containers may determine the impact that the container quality scores of the associated containers may have on the document quality score (e.g., document quality score 214) of the document.

According to one embodiment, the container relevancy scores may be determined based on one or more domain links to a domain knowledge base (e.g., domain knowledge base 210). The domain links may include domain-specific mentions and/or domain-specific contextual clues identified in the containers and matched with data in the domain knowledge base. The quality assessment program 110a, 110b may calculate the container relevancy score of the respective containers based on identifying relevant mention types (e.g., domain-specific mentions and/or domain-specific contextual clues), rare mention types (e.g., specific or niche category of relevant mention type), and a combination of mention types (e.g., combination of relevant and rare mention types) in the associated container. Thereafter, the quality assessment program 110a, 110b may calculate and provide the container relevancy score (e.g., range from 0-1.0, where 0-0.4 may indicate poor relevancy, 0.41-0.7 may indicate fair relevancy, and 0.71-1.0 may indicate good relevancy) for each of the containers.

According to one embodiment, the quality assessment program 110a, 110b may revise the container relevancy score based on the associated container name (e.g., container name 208a). In one embodiment, the quality assessment program 110a, 110b may maintain a relevancy map (e.g., relevancy map 220) which may link container names to container relevancy based on pre-existing knowledge associated with similar container names.

Continuing with the previous example, where example containers 1-4 are provided above in TABLES 1-4, respectively. The quality assessment program 110a, 110b implements lexical matching on container 1 and identifies the terms "we find," "abnormal," "lesion," "right," "lung," and "metastasis" as domain links to the domain knowledge base 210. Thereafter, the quality assessment program 110a, 110b determines a container relevancy score 218 of 1.0 out of 1.0 (good relevancy) due to the frequency/density of the relevant mention types in the container 1.

In container 2, the quality assessment program 110a, 110b identifies the container name 208 "Gross Description." Based on the relevancy map 220, the quality assessment program 110a, 110b determines that "Gross Description" containers provide no relevancy and as such, the quality assessment program 110a, 110b determines a container relevancy score 218 of 0.0 out of 1.0 (poor relevancy) for container 2.

In container 3, the quality assessment program 110a, 110b implements lexical matching and determines a low frequency of domain-specific mentions and/or domain-specific context clues. As such, the quality assessment program 110a, 110b determines a container relevancy score 218 of 0.1 out of 1.0 (poor relevancy) for container 3.

In container 4, the quality assessment program 110a, 110b implements lexical matching and identifies the terms "no acute distress," "ECOG 1," "No palpable peripheral lymphadenopathy," "Clear to auscultation," "no palpable masses," "edema," "swelling," "gait," and "jaundice" as relevant mention types (domain links) associated with the domain knowledge base 210. Thereafter, the quality assessment program 110a, 110b determines a container relevancy score 218 of 1.0 out of 1.0 (good relevancy) due to the frequency/density of the relevant mention types in the container 1.

Thereafter at 306, a document quality score is computed. The quality assessment program 110a, 110b may calculate the document quality score (e.g., document quality score 214) by combining the container quality score (e.g., container quality score 216) and the container relevancy score (e.g., container relevancy score 218) of the respective containers (e.g., containers 208) of the document (e.g., document 204). As previously described, the container relevancy score corresponding to the container quality score may determine the impact that the container quality score may have on the document quality score. Further, as previously described, the container relevancy score may be determined based on one or more domain links to the domain knowledge base. Accordingly, in one embodiment, computing the document quality score may include computing the document quality score based on one or more container relevancy scores determined based on one or more domain links to the domain knowledge base.

According to one embodiment, the quality assessment program 110a, 110b may provide a scored document (e.g., scored document 212) including the container quality score and the container relevancy score of the respective containers. In addition, the quality assessment program 110a, 110b may provide, in the scored document, the document quality score computed based on the container quality scores and the container relevancy scores. In at least one embodiment, the quality assessment program 110a, 110b may determine the document quality score by computing a weighted average of (container_relevancy_score*container_ quality_ score). According to one embodiment, the container relevancy score may be applied as the weight such that higher container relevancy scores may contribute more to the document quality score and lower container relevancy scores may contribute less to the document quality score. In at least one embodiment, the quality assessment program 110a, 110b may calculate the document quality score in the range from 0-1.0, where 0-0.4 may indicate poor document quality, 0.41-0.7 may indicate fair document quality, and 0.71-1.0 may indicate good document quality.

Continuing with the previous example, where example containers 1-4 are provided above in TABLES 1-4, respectively. The quality assessment program 110a, 110b determines that: container 1 ("Diagnosis") has a container quality score of 0.4 and a container relevancy score of 1.0; container 2 ("Gross Description") has a container quality score of 0.0 and a container relevancy score of 0.0; container 3 ("Comments") has a container quality score of 0.2 and a container relevancy score of 0.1; and container 4 ("Physical Examination") has a container quality score of 0.3 and a container relevancy score of 1.0. Thereafter, the quality assessment program 110a, 110b calculates the weighted average of the container quality scores and container relevancy scores as:

$((1.0\times0.4)+(0.0\times0.0)+(0.1\times0.2)+(1.0\times0.3))/(1+0+0.1+1)=0.34285714$. As such, the quality assessment program 110a, 110b determines that the computed document quality score 214 is 0.34285714.

The functionality of a computer may be improved by the quality assessment program 110a, 110b because the quality assessment program 110a, 110b may use the relevancy of subcomponents (e.g., containers) of a document as an indicator for determining the document quality. The quality assessment program 110a, 110b may identify low-fidelity and high-fidelity spans of text in the document and determine the document quality score based on the relevancy of the low-fidelity and high-fidelity spans of text in the document.

Using a generic document quality assessment model, malformed text in a particular container of the document may lower the document's quality score below the threshold of what the computer may consider to be a "good" document, an action that may very well cause a valid document to be filtered out from further processing. However, using the quality assessment program 110a, 110b, the computer may identify the specific container including the malformed text and determine the potential relevancy of that specific container to the overall meaning and understanding of the document. If the quality assessment program 110a, 110b determines that the malformed text does not include mentions that may be relevant to a specific domain or if the quality assessment program 110a, 110b determines, from pre-existing knowledge, that the specific container having the malformed text is "noise," the quality assessment program 110a, 110b may determine that the malformed text has no bearing on the intended understanding of the document and therefore would not lower the document quality score based on the malformed text. As such, the computer may not filter out the otherwise valid document based on the granular document quality assessment provided by the quality assessment program 110a, 110b.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Figure 4:
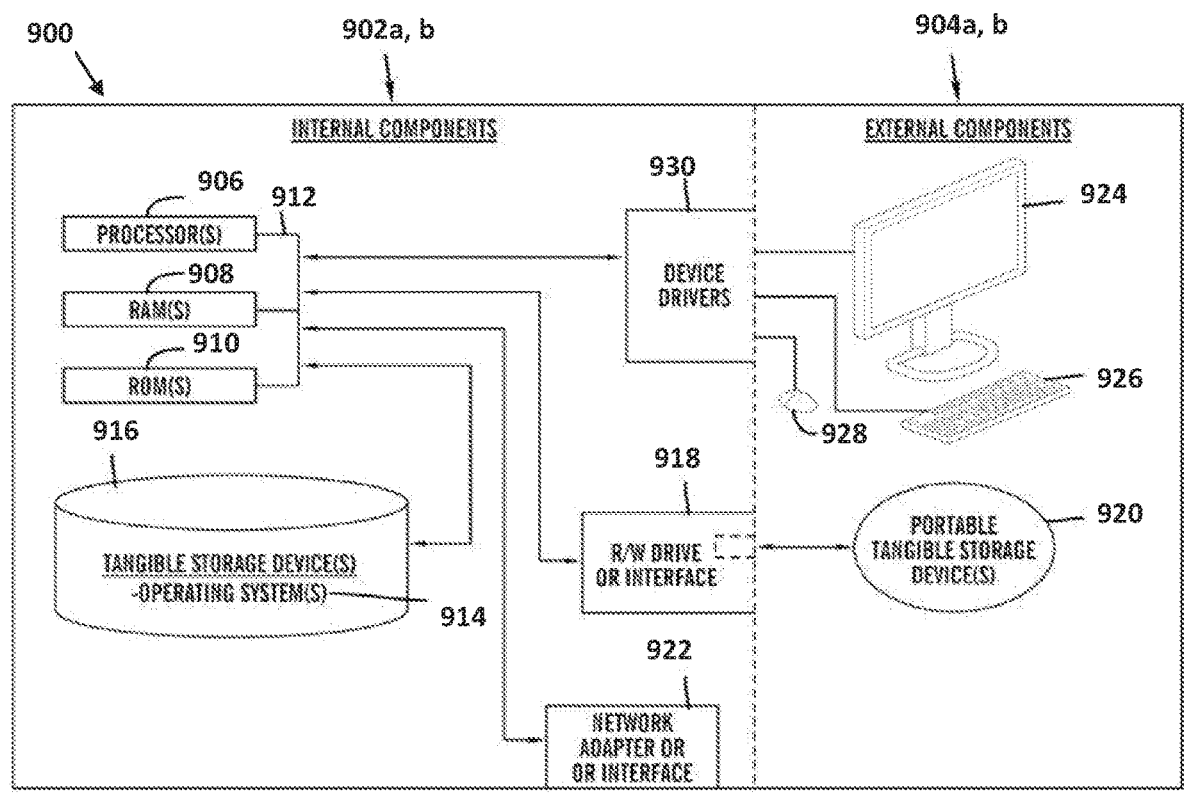
FIG. 4 is a block diagram of internal and external components of computers and servers depicted in FIG. 1 according to at least one embodiment.

FIG. 4 is a block diagram 900 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 4. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the quality assessment program 110a in client computer 102, and the quality assessment program 110b in network server 112, may be stored on one or more computer-readable tangible storage devices 916 for execution by one or more processors 906 via one or more RAMs 908 (which typically include cache memory). In the embodiment illustrated in FIG. 4, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the quality assessment program 110a and 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the quality assessment program 110a in client computer 102 and the quality assessment program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the quality assessment program 110a in client computer 102 and the quality assessment program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
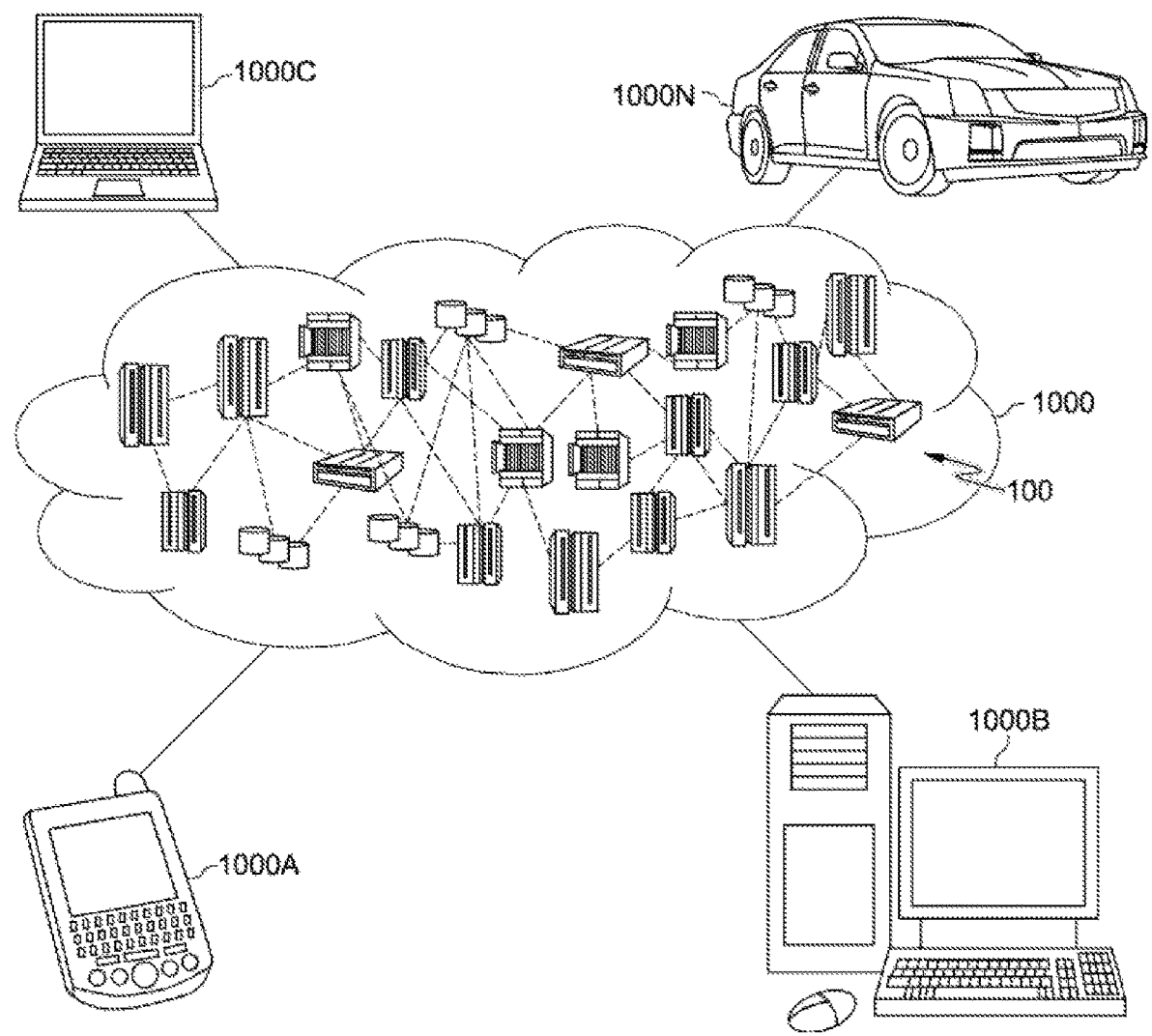
FIG. 5 is a block diagram of an illustrative cloud computing environment including the computer system depicted in FIG. 1, in accordance with an embodiment of the present disclosure.

Referring now to FIG. 5, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 5 are intended to be illustrative only and that computing nodes 100 and cloud computing environment 1000 can communicate with any type of computerized device over any type of network and/or network addressable connection (e.g., using a web browser).

Figure 6:
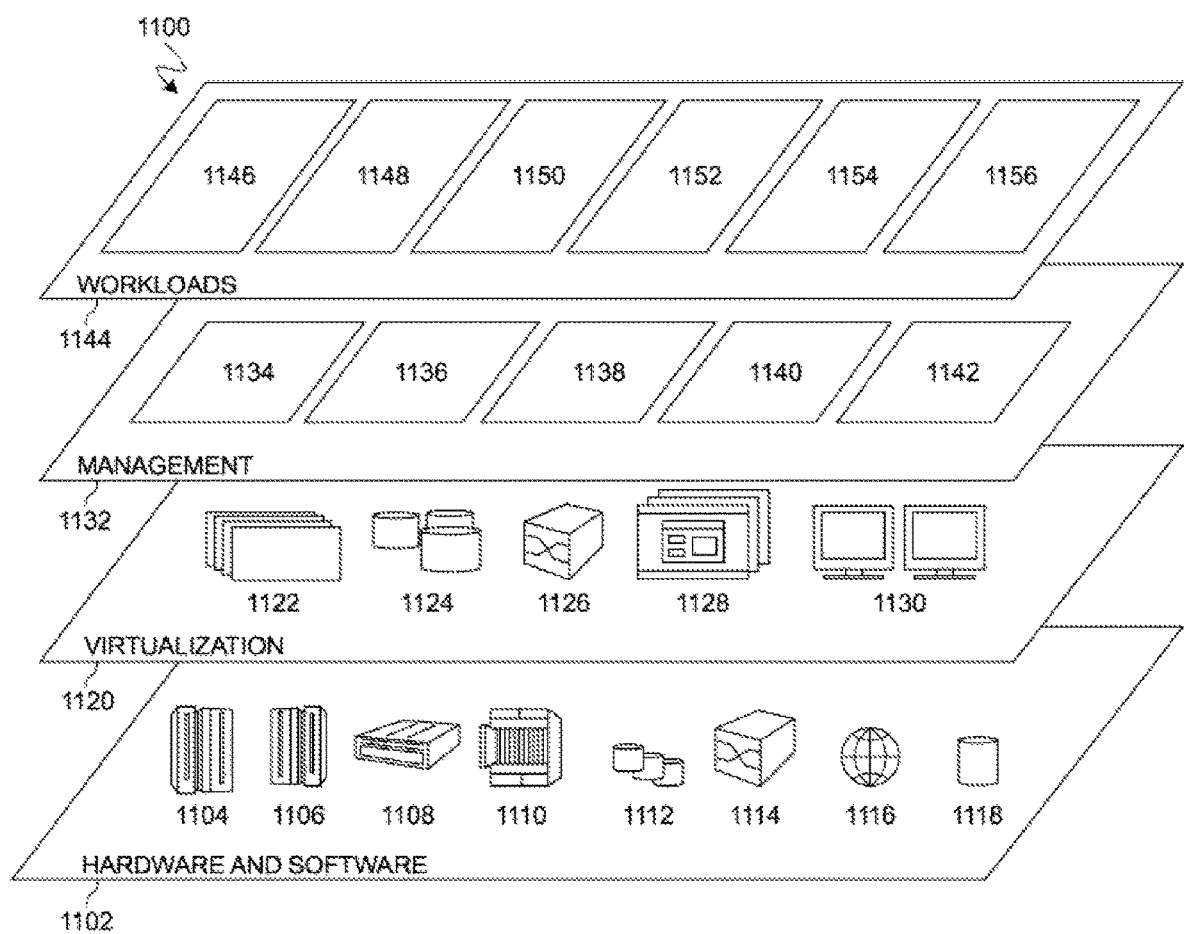
FIG. 6 is a block diagram of functional layers of the illustrative cloud computing environment of FIG. 5, in accordance with an embodiment of the present disclosure.

Referring now to FIG. 6, a set of functional abstraction layers 1100 provided by cloud computing environment 1000 is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124;

virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and quality assessment 1156. A quality assessment program 110a, 110b provides a way to compute a document quality score based on one or more container relevancy scores determined based on one or more domain links to a domain knowledge base.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   computing a document quality score based on at least one container relevancy score associated with a container of a document determined based on at least one domain link to a domain knowledge base;
   identifying a container name associated with the container;
   mapping, based on a relevancy map of container names linked to container relevance, the identified container name to a pre-determined container relevancy; and
   revising the at least one container relevancy score based on the mapped container name associated with the pre-determined container relevancy.

2. The method of claim 1, wherein computing the document quality score based on the at least one container relevancy score determined based on the at least one domain link to the domain knowledge base further comprises:
   computing the document quality score based on the at least one container relevancy score and at least one container quality score determined based on at least one document quality heuristic.

3. The method of claim 2, wherein the at least one document quality heuristic is selected from the group consisting of a percentage of valid characters, a percentage of valid words, a percentage of complete sentences, a number of irrelevant tags, a number of blank spaces between sentences, and a number of blank spaces between tokens.

4. The method of claim 2, further comprising:
   determining a weight of the at least one container quality score for the computed document quality score based on the at least one container relevancy score corresponding to the at least one container quality score.

5. The method of claim 1, wherein computing the document quality score based on the at least one container relevancy score determined based on the at least one domain link to the domain knowledge base further comprises:
   determining at least one container quality score corresponding to the at least one container relevancy score; and
   computing a weighted average of the at least one determined container quality score and the at least one container relevancy score.

6. The method of claim 5, further comprising:
   displaying, using a graphical user interface (GUI), a digital representation of a scored document including at least one annotated container indicating the at least one container relevancy score, the at least one determined container quality score corresponding to the at least one container relevancy score, and the computed document quality score.

7. The method of claim 1, further comprising:
   determining, based on at least one document quality heuristic, at least one container quality score associated with at least one respective container of a document; and
   determining the at least one container relevancy score based on identifying the at least one domain link to the domain knowledge base in the at least one respective container of the document.

8. The method of claim 7, wherein determining the at least one container relevancy score based on identifying the at least one domain link to the domain knowledge base in the at least one respective container of the document further comprises:
   performing lexical matching between the at least one respective container of the document and the domain knowledge base.

9. The method of claim 1, further comprising:
   accessing a document from a document corpus;
   normalizing the accessed document; and
   identifying at least one container in the normalized document.

10. The method of claim 9, wherein the at least one container is selected from the group consisting of a section, a subsection, a paragraph, a sentence, and a list.

11. The method of claim 9, wherein normalizing the accessed document further comprises:
    removing at least one non-text object from the accessed document; and
    extracting at least one span of text from the accessed document into a plain text file.

12. The method of claim 11, further comprising:
    highlighting, using the GUI in the displayed digital representation of the scored document, the at least one annotated container most impacting the computed document quality score.

13. The method of claim 1, wherein the at least one domain link to the domain knowledge base is selected from a group consisting of a relevant mention type, a rare mention type, and a combination of mention types.

14. A computer system for relevancy-based document quality assessment, comprising:
one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is capable of performing a method comprising:
computing a document quality score based on at least one container relevancy score associated with a container of a document determined based on at least one domain link to a domain knowledge base;
identifying a container name associated with the container;
mapping, based on a relevancy map of container names linked to container relevance, the identified container name to a pre-determined container relevancy; and
revising the at least one container relevancy score based on the mapped container name associated with the pre-determined container relevancy.

15. The computer system of claim 14, wherein computing the document quality score based on the at least one container relevancy score determined based on the at least one domain link to the domain knowledge base further comprises:
computing the document quality score based on the at least one container relevancy score and at least one container quality score determined based on at least one document quality heuristic.

16. The computer system of claim 14, wherein computing the document quality score based on the at least one container relevancy score determined based on the at least one domain link to the domain knowledge base further comprises:
determining at least one container quality score corresponding to the at least one container relevancy score; and
computing a weighted average of the at least one determined container quality score and the at least one container relevancy score.

17. The computer system of claim 14, further comprising:
determining, based on at least one document quality heuristic, at least one container quality score associated with at least one respective container of a document; and
determining the at least one container relevancy score based on identifying the at least one domain link to the domain knowledge base in the at least one respective container of the document.

18. The computer system of claim 14, further comprising:
accessing a document from a document corpus;
normalizing the accessed document; and
identifying at least one container in the normalized document.

19. A computer program product for relevancy-based document quality assessment, the computer program product comprising a computer readable storage medium having program instructions embodied therewith, the program instructions executable by a processor to cause the processor to perform a method comprising:
computing a document quality score based on at least one container relevancy score associated with a container of a document determined based on at least one domain link to a domain knowledge base;
identifying a container name associated with the container;
mapping, based on a relevancy map of container names linked to container relevance, the identified container name to a pre-determined container relevancy; and
revising the at least one container relevancy score based on the mapped container name associated with the pre-determined container relevancy.

\* \* \* \* \*